United States Patent [19]
Buchholz et al.

[11] Patent Number: 5,440,028
[45] Date of Patent: Aug. 8, 1995

[54] PROCESS FOR PREPARING PURIFIED GLYCOLIPIDS BY MEMBRANE SEPARATION PROCESSES

[75] Inventors: Rainer Buchholz, Berlin; Ulrich Fricke; Johann Mixich, both of Kelkeim, all of Germany

[73] Assignee: Hoechst Aktiengesellschaft, Frankfurt am Main, Germany

[21] Appl. No.: 257,445

[22] Filed: Jun. 8, 1994

Related U.S. Application Data

[63] Continuation of Ser. No. 30,090, filed as PCT/EP91/01756, Sep. 14, 1991, abandoned.

[30] Foreign Application Priority Data

Sep. 25, 1990 [DE] Germany ............... 40 30 264.4

[51] Int. Cl.$^6$ ............... C07H 1/06; C07H 3/00
[52] U.S. Cl. ............... 536/124; 536/127
[58] Field of Search ............... 536/127, 124

[56] References Cited

U.S. PATENT DOCUMENTS

| | | | |
|---|---|---|---|
| 4,812,272 | 3/1989 | Heinrich et al. | 264/65 |
| 4,814,272 | 3/1989 | Wagner et al. | 536/18.2 |
| 5,032,281 | 7/1991 | Nagamatsu et al. | 210/651 |

FOREIGN PATENT DOCUMENTS

0282942A2  9/1988  European Pat. Off.

OTHER PUBLICATIONS

Trehalose Lipid and α-Branched-β-hydroxy Fatty Acid Formed by Bacteria Grown on n–Alkanes, Suzuki et al., Agr. Biol. Chem., 33(11):1619–1627 (1969).

Surface-Active Compounds from Microorganisms, Cooper et al., Advances in Applied Microbiology, 26:229–259 (1980).

Chemical and Physical Characterization of Four Interfacial-Active Rhamnoplipids From Pseudomonas Spec. DSM 2874 Grown on n-Alkanes, Syldatk et al., Z. Naturforsch, 40:51–60 (1985).

Production of Four Interfacial Active Rhamnolipids From n-Alkanes or Glycerol by Resting Cells of Pseudomonas Species DSM 2874, Syldatk et al., Z. Naturforsch, 40:61–67 (1985).

Recovery of Biosurfactants by Ultrafiltration, Mulligan et al., J. Chem. Tech. Biotechnol., 47:23–29 (1990).

*Primary Examiner*—Michael G. Wityshyn
*Assistant Examiner*—Everett White
*Attorney, Agent, or Firm*—Finnegan, Henderson, Farabow, Garrett & Dunner

[57]  ABSTRACT

Process for preparing purified glycolipids by membrane separation processes. Glycolipids may be purified and concentrated using a membrane separation process at acid pH and employing a membrane with a cut-off size of 30,000.

16 Claims, No Drawings

PROCESS FOR PREPARING PURIFIED GLYCOLIPIDS BY MEMBRANE SEPARATION PROCESSES

This application is a continuation of application Ser. No. 08/030,090 filed as PCT/EP91/01756, Sep. 14, 1991, now abandoned.

Glycolipids are composed of a fatty acid residue and a sugar residue. One of the best-known glycolipids is trehalose lipid (Suzuki et al., 1969, Agric. Biol. Chem., 33, 1619–1627). It is composed of the disaccharide trehalose and two β-hydroxy α-branched fatty acids (corynomycolic acid) which are esterified by hydroxyl groups of the sugar. Glycolipids that contain rhamnose and β-hydroxy fatty acids are described in EP 0 153 634. The first rhamnolipid to have its structure determined comprises two molecules of L-rhamnose and two molecules of β-hydroxydecanoic acid (Ewards and Hayashi, 1965, Arch. Biochem. Biophys., 111, 415–421).

The glycolipids known hitherto have a molecular weight between 250 and 2000, in each case depending on the sugar moiety and the fatty acid moiety. They are secreted into the surrounding nutrient medium by bacteria, for example, and can be accumulated as a mixture of several different glycolipids (EP 0 153 634; Advances in Appl. Microbiol. 1980, 229–259).

Glycolipids can be used, for example, as emulsifiers, biosurfactants or stabilizers for emulsions.

The processes for purifying glycolipids are based on extraction, crystallization and chromatographic processes (EP 0 282 942; U.S. Pat. No. 4 814,272). However, large quantities of solvents accumulate in these processes. Mulligan and Gibbs (J. Chem. Tech. Biotechnol. 1990, 47, 23–29) describe an ultrafiltration process for purifying biosurfactants, such as surfactin and rhamnolipids. However, the retention ability of the membranes described in that paper decreases with increasing pore size. In the case of membranes with a cut-off size of 30,000, this leads to glycolipid losses of more than 77%.

It has now been found, surprisingly, that, at acid pH, glycolipids are virtually completely retained by a membrane that has a cut-off size for molecules with a molecular weight of more than 30,000.

The invention consequently relates to a process for preparing purified glycolipids which is characterized in that the purification is carried out using a membrane separation process at acid pH with a membrane which has a cut-off size for molecules with a molecular weight of more than 30,000.

The invention is described in detail below, in particular in its preferred embodiments.

Glycolipids can occur in plants or bacteria (Lehninger, Biochemistry, 1977; Syldakt et al., Z. Naturforschung, 40 c, 1985, 51–67). Fermentations preferably come into consideration for preparing glycolipids. For this purpose, the microorganisms are cultured in a manner known per se. The glycolipids which are secreted into the culture medium are, for example, purified at the end of the fermentation using the membrane separation process according to the invention, preferably ultrafiltration. The ultrafiltration can be carried out, for example, with equipment using plates, tubes, capillary tubes, spiral membranes or hollow fibers, containing membranes with a cut-off size of 30,000 to 300,000. Membranes are preferably employed with a cut-off size of 100,000 to 200,000. The cut-off size relates to the molecular weight of the molecules to be retained and means that substances with a molecular weight greater than the stated value are retained. Polysulfones, polyamides or cellulose acetates may be used as the membrane material. The glycolipids are retained by the membrane and can be processed further after the purification.

The membrane separation process according to the invention is carried out at an acid pH, preferably at a pH of 1 to 5, particularly preferably at a pH of 2 to 4. Adjustment of pH is effected, if necessary, using an acid or an alkali. Hydrochloric acid, sulfuric acid, acetic acid, citric acid, sodium hydroxide or sodium carbonate may be used, for example.

The process according to the invention is advantageously employed for the purification of rhamnolipids. The purification of α-L-rhamnopyranosyl-β-hydroxydecanoic acid, 2-O-α-L-rhamnopyranosyl-α-L-rhamnopyranosyl-β-hydroxydecanoic acid, 2-O-α-L-rhamnopyranosyl-α-L-rhamnopyranosyl-β-hydroxydecanoyl-β-hydroxydecanoic acid or α-L-rhamnopyranosyl-β-hydroxydecanoyl-β-hydroxydecanoic acid is particularly preferred.

The purification of glycolipids with an ultrafiltration system can be carried out batchwise or continuously. The temperature of the filtration solution is kept between 0° C. and 70° C., preferably between 18° C. and 40° C.

The velocity of flow of the fluid over the membrane is kept between 2 and 7 m/s, preferably between 5 and 6 m/s. The excess pressure of the fluid at the input to the filtration appliance amounts to between 3 and 6 bar. The pressure drop over the filtration distance lies between 0.5 and 3.5 bar.

The membrane separation process according to the invention may naturally be used not only for purifying glycolipids but also for concentrating them.

Example 1

Pseudomonas spec. DSM 2874 was cultured under aerobic conditions in a nutrient solution using paraffin S (89% tetradecane, 9% pentadecane) as carbon source, in accordance with German Patent 3 405 664. The fermentation was effected at a pH of 6.6 and 7.2, and at 30° C. with an aeration rate of 0.2 V/V/m. The fermentation had finished after 7 days. The fermentation solution contained a rhamnose-lipid mixture with an L-rhamnose component of 2.5 g/l.

EXAMPLE 2

The fermentation solution obtained from Example 1 was adjusted to pH 3 with sulfuric acid and subsequently concentrated in a modular tube-ultrafiltration system (Böttcher, Austria). The following operational parameters were maintained:

| | |
|---|---|
| Input pressure | 5 bar |
| Output pressure | 1.5 bar |
| Temperature | 35° C. |
| Flow-over velocity | 5 m/s |
| Filtration performance | 200 l/h |
| Concentration factor | 3.9 |
| Initial volume | 18.6 m$^3$ |
| Final volume | 4.8 m$^3$ |

After the concentration, the concentrate contained a rhamnose-lipid mixture with an L-rhamnose component of 9.75 g/l.

EXAMPLE 3

The concentrated fermentation solution obtained from Example 2 was desalted with water by diafiltration at pH 3 and constant volume. A modular tube-ultrafiltration system (Böttcher, Austria) was used for this purpose. The UF-PS-100 polysulfone membrane, from Kalle-Albert, Wiesbaden, had a cut-off size of 100,000. The following operational parameters were maintained:

| | |
|---|---|
| Input pressure | 5 bar |
| Output pressure | 1.5 bar |
| Temperature | 35° C. |
| Flow-over velocity | 5 m/s |
| Filtration performance | 59 l/m$^2$h |
| Volume of the solution | 4.8 m$^3$ |

The fermentation broth had a conductivity of 24.5 mS cm$^{-1}$ before desalting and 2.9 mS cm$^{-1}$ thereafter. The permeate contained 0.1 g/l L-rhamnose.

EXAMPLE 4

For comparison, a fermentation solution containing rhamnose lipid was passed over membranes with cut-off sizes of 10,000 and 100,000, respectively:

| Operational parameters: | | |
|---|---|---|
| Flow over | 0.3 m$^3$/h | |
| Output pressure | 4 bar | |
| Temperature | 32° C. | |
| Membrane area | 0.45 m$^2$ | |
| pH | 3 | |
| Membrane types | Permeate | Flux l/m$^2$h |
| Polysulfone 10,000 D | Clear | 0.8 |
| Polysulfone 100,000 D | Clear | 50.0 |

In both cases the retention of rhamnolipid was 99%.

We claim:

1. A process for preparing purified glycolipids wherein the purification is carried out using a membrane separation process at acid pH with a membrane which has a cut-off size of molecules with a molecular weight of more than 30,000.

2. A process according to claim 1 wherein the glycolipids are rhamnolipids.

3. A process according to claim 1 wherein the glycolipids are selected from the group consisting of α-L-rhamnopyranosyl-β-hydroxydecanoic acid, 2-O-α-L-rhamnopyranosyl-α-L-rhamnopyranosyl-β-hydroxydecanoic acid, 2-α-L-rhamnopyranosyl-α-L-rhamnopyranosyl-β-hydroxydecanoyl-β-hydroxydecanoic acid and α-L-rhamnopyranosyl-β-hydroxydecanoyl-β-hydroxydecanoic acid.

4. A process according to claim 1 wherein ultrafiltration serves as the membrane separation process.

5. A process according to claim 4 wherein an ultrafiltration membrane with a cut-off size of 30,000 to 300,000 is employed.

6. A process according to claim 5 wherein an ultrafiltration membrane with a cut-off size of 100,000 to 200,000 is employed.

7. A process according to claim 4 wherein the process is carried out at a pH of 1 to 5.

8. A process according to claim 7 wherein the process is carried out at a pH of 2 to 4.

9. A process according to claim 8 wherein the process is carried out at a temperature of 0° to 70° C.

10. A process according to claim 7 wherein the process is carried out at a temperature of 0° to 70° C.

11. A process according to claim 4 wherein the process is carried out at a temperature of 0° to 70° C.

12. A process according to claim 1 wherein the process is carried out at a pH of 1 to 5.

13. A process according to claim 12 wherein the process is carried out at a pH of 2 to 4.

14. A process according to claim 13 wherein the process is carried out at a temperature of 0° to 70° C.

15. A process according to claim 12 wherein the process is carried out at a temperature of 0° to 70° C.

16. A process according to claim 1 wherein the process is carried out at a temperature of 0° to 70° C.

* * * * *

UNITED STATES PATENT AND TRADEMARK OFFICE
CERTIFICATE OF CORRECTION

PATENT NO. : 5,440,028
DATED : August 08, 1995
INVENTOR(S) : Rainer BUCHHOLZ et al.

It is certified that error appears in the above-indentified patent and that said Letters Patent is hereby corrected as shown below:

Claim 3, column 4, line 9, between "2-" and "α-", insert --0- --.

Signed and Sealed this

Ninth Day of July, 1996

Attest:

BRUCE LEHMAN

*Attesting Officer*       *Commissioner of Patents and Trademarks*